United States Patent
Olson

(10) Patent No.: US 6,847,301 B1
(45) Date of Patent: Jan. 25, 2005

(54) PATIENT POSITION MONITORING DEVICE

(75) Inventor: Richard T. Olson, Cedar Rapids, IA (US)

(73) Assignee: Personal Safety Corporation, Cedar Rapids, IA (US)

( * ) Notice: Subject to any disclaimer, the term of this patent is extended or adjusted under 35 U.S.C. 154(b) by 11 days.

(21) Appl. No.: 10/248,983

(22) Filed: Mar. 6, 2003

(51) Int. Cl.[7] .............................................. G08B 21/00
(52) U.S. Cl. ................ 340/666; 340/573.1; 340/573.4; 340/686.1; 200/85 R
(58) Field of Search ............................... 340/666, 575, 340/686.1, 687, 573.4, 573.1, 573.3; 200/85 R

(56) References Cited

U.S. PATENT DOCUMENTS

| | | | |
|---|---|---|---|
| 4,020,482 A | | 4/1977 | Feldl |
| 4,638,307 A | * | 1/1987 | Swartout .................... 340/666 |
| 4,907,845 A | * | 3/1990 | Wood ...................... 340/573.4 |
| 5,140,309 A | | 8/1992 | Gusakov |
| 5,796,059 A | | 8/1998 | Boon |
| 5,844,488 A | * | 12/1998 | Musick .................... 340/573.4 |
| 5,990,799 A | | 11/1999 | Boon et al. |
| 6,078,261 A | * | 6/2000 | Davsko ................... 340/573.4 |
| 6,166,644 A | | 12/2000 | Stroda |
| 6,297,738 B1 | * | 10/2001 | Newham ................. 340/573.1 |
| 6,646,556 B1 | * | 11/2003 | Smith et al. ............. 340/573.1 |

* cited by examiner

*Primary Examiner*—Davetta W. Goins
(74) *Attorney, Agent, or Firm*—Ryan N. Carter

(57) ABSTRACT

The disclosed invention is a patient monitoring system that employs a pressure sensitive pad. The pad is placed beneath a patient who is lying in bed or sitting in a chair. When weight is removed from the pad, an alarm is given. The pad comprises an upper layer of circuitry and a lower layer of circuitry. When the respective layers of circuitry are in contact, the alarm remains off, but when the layers of circuitry become separated, the alarm is given. This invention is generally for use in hospitals and nursing homes to alert caregivers when a patient falls out of a bed or a wheelchair; or if a patient otherwise leaves a bed or chair against the wishes of the caregiver. This situation is of special concern with elderly patients, post operational patients, and/or at night when nursing staffs are reduced.

20 Claims, 5 Drawing Sheets

PATIENT POSITION MONITORING DEVICE

BACKGROUND OF INVENTION

The present invention relates to a patient monitoring system, and more particularly to a pressure sensitive pad that sounds an alarm when weight is removed from it. There are many individuals who are physically challenged that are confined to beds or wheelchairs because of illness, disability, or age. Many of these people require assistance in living, but typically they cannot be continuously monitored throughout the day and night. If a patient attempts to leave a bed or chair, or falls out of a bed or chair, they may lie unconscious for a period of time endangering their health and life. To aid in the care of these individuals, medical safety devices have been developed that sound an alarm when a person falls or wanders off against the wishes of the caregiver. The noise produced by these safety devices alerts nurses or other aid personnel that the patient is in need of assistance.

There are a variety of prior art devices that are used to monitor patients. In one type of system, one end of a cord is securely attached to a patient with the other end of the cord being attached to an alarm system. When the patient moves beyond the length of the cord, the cord is pulled free from the alarm system. This causes an audible alarm to be given. This type of system is disclosed in U.S. Pat. Nos. 4,577,185; 4,583,084; and 6,239,704.

Another prior art device for monitoring patients comprises a pressurized fluid that is contained in members that are attached to the side rails of a bed. When a patient attempts to gets out of bed, the patient will typically grasp the side rails, which activates an alarm. However, this device does not provide a warning when a patient falls out of bed involuntarily, or when the bed is not provided with suitable side rails.

There have also been a number of pressure sensitive pads disclosed in prior art. One such pad is Feldl (U.S. Pat. No. 4,020,482). Feldl teaches a flexible bag that is placed below a mattress of a bed in a hospital or nursing home. When weight is removed from the bag, pressure in the bag is lost and a switch is activated, giving a signal at the attendant's station. The problem with this type of device is that it may be difficult to set the pressure in the bag correctly. Different mattresses and different patients weigh different amounts, and thus if the bag pressure is not set correctly, the alarm may be given at the wrong times, or not given at the proper times.

There is therefore a need for a pressure sensitive pad that can produce a warning to caregivers when a patient moves from a chair or bed either voluntarily or involuntarily.

SUMMARY OF INVENTION

The invention provides a device that comprises a pad on which a patient sits or lays. When the patient's weight is removed from the pad, an alarm sounds giving an audible warning to nearby caregivers. Inside the pad there is circuitry, which is connected to an external alarm system by a cord. The circuitry of the pad is positioned in a grid pattern throughout the entire pad and is enclosed in a transparent plastic film. The film is folded in half, creating an upper layer of circuitry and a lower layer of circuitry. Between the layers of circuitry is a resilient material such as sponge. When weight is applied to the pad, air in the pad and sponge exit the interior of the pad through air holes, causing the top layer of circuitry to come into contact with the bottom layer, which keeps the alarm from sounding. However, when weight is removed from the pad, air enters the pad and sponge through the air holes, causing the two layers of circuitry to become separated, which causes the alarm to sound.

The pad is comprised of a heavy duty, waterproof outer cover such as polyvinyl chloride (PVC) that allows the pad to withstand constant daily usage. It is important that the pad is waterproof since liquid can cause electrical devices to short circuit. It is particularly important that patient safety devices be waterproof since medical patients and elderly people may have more of a tendency to spill if they are in a weakened state. Furthermore, waterproofing is important because patients and elderly people may be incontinent. Therefore, the few openings that the pad does have are designed in such a way so as to minimize the likelihood of liquid contacting the circuitry.

The pad has an inside layer of corrugated plastic sheeting that adds rigidity to the pad. This allows the pad to function even if used on a soft mattress or if used by a lighter weight patient.

It is thus an object of this invention to provide a simple, cost effective way to monitor patients in their beds or wheelchairs.

It is further an object of this invention to provide a patient monitoring pad that has circuitry in a grid pattern throughout the pad which allows the device to function properly no matter where pressure is applied on its surface.

It is further an object of this invention to provide a patient monitoring system that continues to function properly even if it comes into contact with liquid.

It is further an object of this invention to provide a patient monitoring pad that functions properly even on soft mattresses or if used by lighter weight patients.

It is further an object of this invention to provide a patient monitoring pad that comprises slip-resistant cushions to kept he pad in position to maintain efficiency of use.

DETAILED DESCRIPTION

Figure 1:
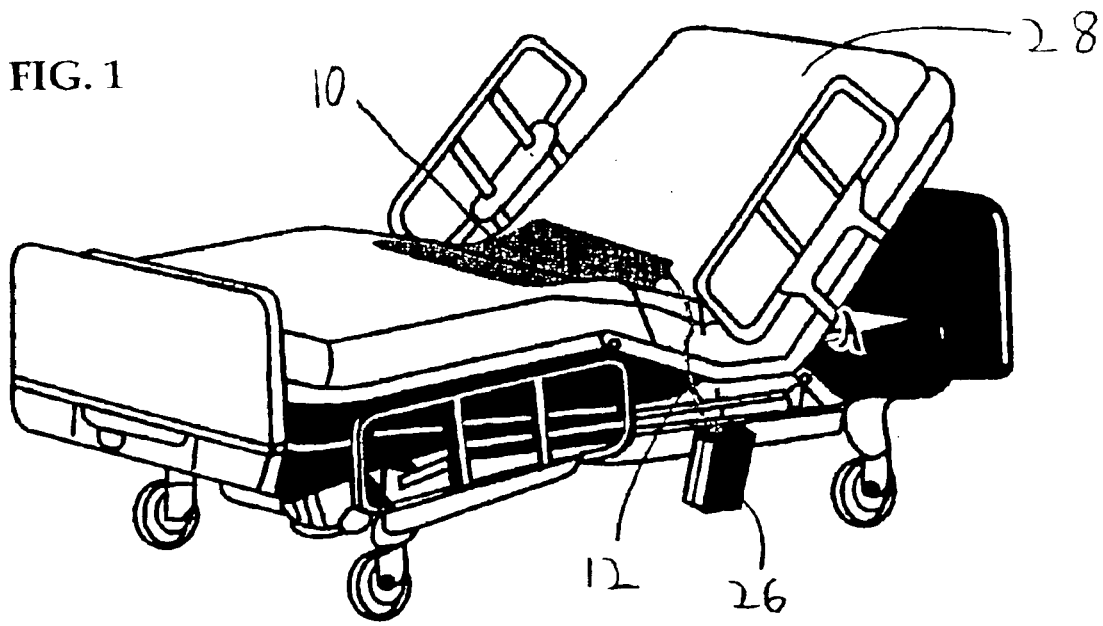
FIG. 1 is a perspective view illustrating a bed with the device of the invention lying on the bed, and an alarm attached to the bed frame.
Figure 2:
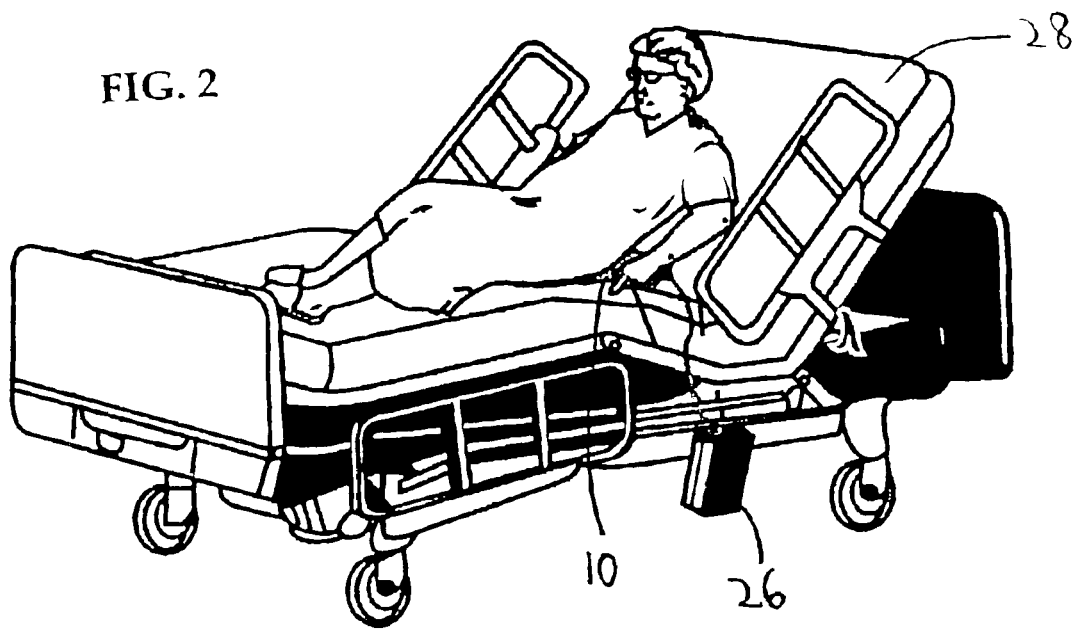
FIG. 2 is a perspective view illustrating an individual lying in bed with the device of the invention underneath them, and an alarm attached to the bed frame.

In FIGS. 1 and 2 of the drawings there is illustrated a bed 28 that has rails as is well known. In FIG. 1 the pressure pad 10 is shown positioned on the bed 28 with the cord 12 running to the alarm 26 base, containing a power source. FIG. 2 illustrates a patient lying on the pressure pad 10. If the alarm 26 is turned to the "on" position, and the patient falls or otherwise moves off of the pressure pad 10, the alarm 26 will issue to alert caregivers of the potentially dangerous situation.

Figure 3:
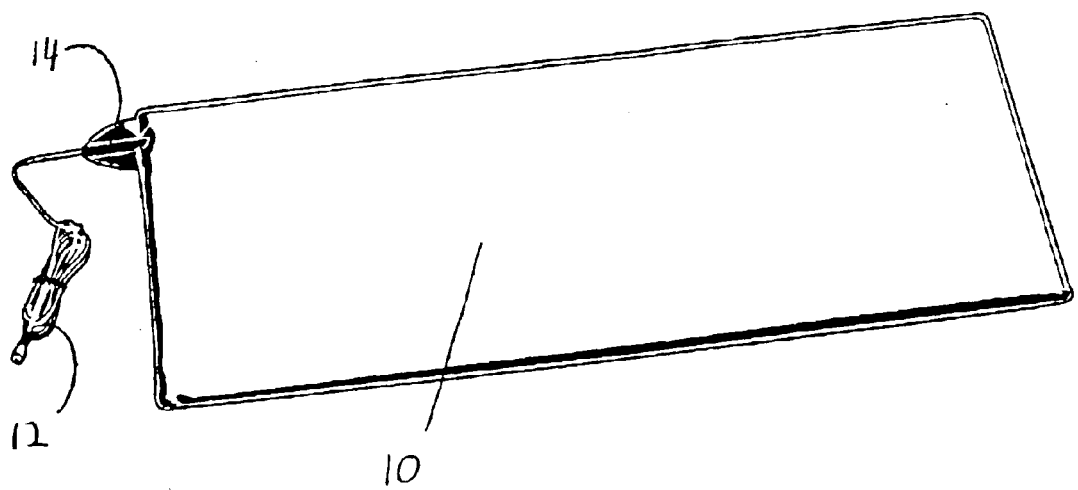
FIG. 3 is a perspective view of the top side of the bed embodiment of the invention.
Figure 4:
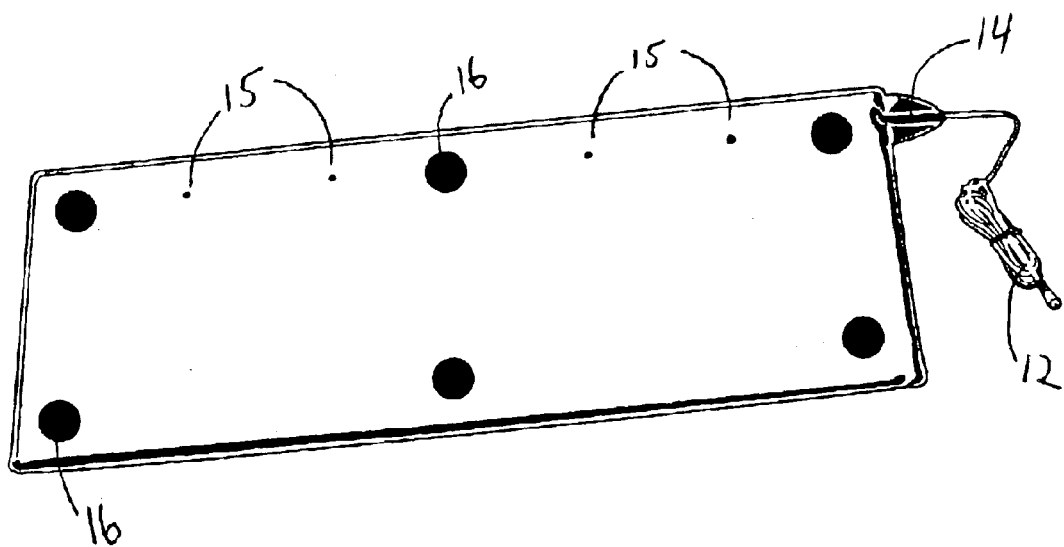
FIG. 4 is a perspective view of the bottom side of the bed embodiment of the invention.

The first embodiment of this invention is shown in FIGS. 3 and 4, which illustrate the top and bottom of the bed pressure pad 10 embodiment of the invention. The bed pressure pad 10 embodiment of the present invention is elongated so as to be placed underneath a patient's body as they lie in bed. The outside of the pad 10 is comprised of a heavy duty cover such as PVC that allows the pad 10 to be durable and withstand constant daily usage. FIG. 4 shows how the bottom of the pad 10 contains several slip retardant cushions 16, which keep the pad 10 from sliding out from under the patient.

Figure 7:
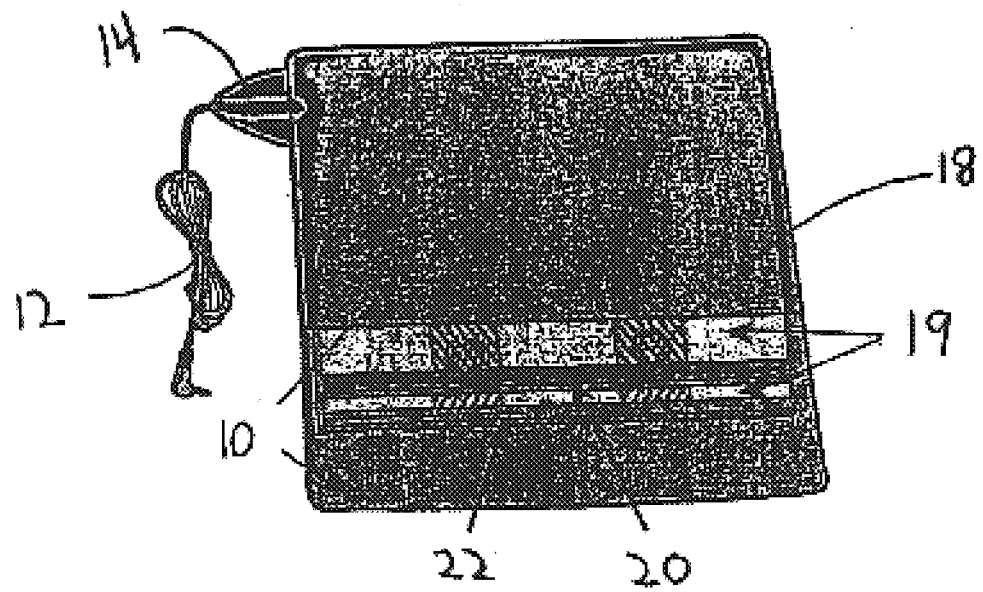
FIG. 7 is a cross-sectional view of the pad and its inner components.

FIG. 7 shows a cross-sectional view of the elements inside the pad 10. The circuitry 18 is folded in half so as to create an upper layer of circuitry and a lower layer of circuitry. There is a resilient material such as a high-density sponge 20 inserted between the layers of circuitry 18. This sponge 20 keeps the upper and lower layers of circuitry separated when no weight is on the pad 10. In order for the circuitry 18 inside the pad 10 to open and close properly, the pad 10 contains air holes 15, as shown in FIG. 4. These air holes 15 allow air to enter and exit the pad 10 in relation to how much weight is on the pad 10. As the patient sits on the pad 10, the pad 10 and sponge 20 are compressed and the pad 10 is able to lose air through the air holes 15 causing the top and bottom layers of circuitry 18 to come into contact with each other. In this position the alarm 26 does not sound. As the patient's weight is removed from the pad 10, the sponge 20 expands, causing air to enter through the air holes 115 allowing the pad 10 to expand or "recover," during which time the top and bottom layers of circuitry 18 become separated, causing the alarm 26 to sound.

When weight is removed from the pad 10 and, consequently, the top and bottom layers of circuitry become separated, there is a short delay before the alarm 26 sounds so as to minimize the potential for false alarms. This delay can be designed into the circuitry of the alarm system or it can be a pneumatic delay caused by the slow expansion of the sponge 20. This delay allows the patient to change positions or otherwise get comfortable. If the alarm 26 begins to sound because weight is removed from the pad 10, and subsequently the patient lies back down on the pad 10, the alarm 26 will cease and automatically reset for the next incident.

One concern with electrical devices is that they can short circuit if they are exposed to liquids. In regards to patient safety devices this is a concern since medical patients or elderly people may be in a weakened state or they may be dizzy, thus increasing their likelihood to spill food or drink. This is also a concern for patients that are incontinent. The present invention makes electrical short-circuiting nearly impossible through several design aspects shown in FIGS. 3 and 4. The primary waterproofing element is the outer vinyl layer of the pad 10. Applicant's invention requires several openings to be in the outer vinyl layer for reasons discussed herein; however, Applicant's device has unique design features that reduce the likelihood that liquid will contact the circuitry 18. The first required opening in the outer layer is at the point where the alarm cord 12 exits the pad for connection to the alarm 26 base. This opening is protected by providing a "V" shaped extension 14 of the heavy-duty cover. This "V" shaped extension travels a short distance along the alarm cord 12 after the alarm cord 12 leaves the pad 10. In the preferred embodiment, this "V" shaped extension 14 is flexible and can be pointed downward. In this downward position, any liquid that is spilled onto the pad 10 runs down the "V" shaped extension 14 and off of the pad 10, without being able to enter the interior of the pad 10. A second design element that requires openings in the outer cover is the air holes 15. The circuitry 18 is protected from any liquid that may enter into the air holes 15 because the corrugated plastic sheet 22 is located between the air holes 15 and the circuitry 18. This makes it nearly impossible for a sufficient amount of liquid to enter the small air holes 18, travel around the corrugated plastic sheet 22 and reach the circuitry 18 on the opposite side so as to create a short circuit. Lastly, the circuitry 18 is enclosed in a transparent plastic film 19 which protects it from contact with any liquid that may get into the pad 10.

Figure 9:
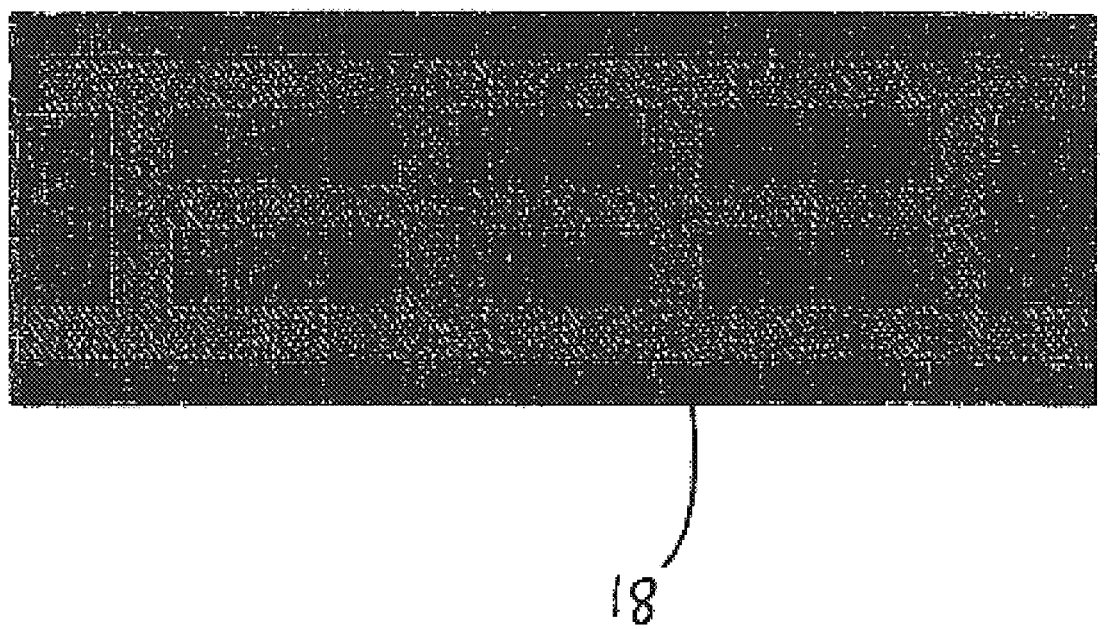
FIG. 9 is a cross-sectional view of the circuitry of the invention.

FIG. 7 and FIG. 9 show the inside circuitry 18 of the pad. It is the circuitry 18 of the pad 10 that acts as the switch to engage and disengage the alarm 26. Using the circuitry 18 as the switch to activate the alarm 26 is advantageous over other types of switches because the circuitry 18 is very thin, and thus cannot be felt by patients as they often have to remain on the pad 10 for long periods of time. FIG. 9 shows how the pressure sensitive circuitry 18 of the pad 10 is laid in a pattern throughout the pad 10 so the alarm system will function no matter where pressure is applied or released on the entire surface of the pad 10.

Figure 8:
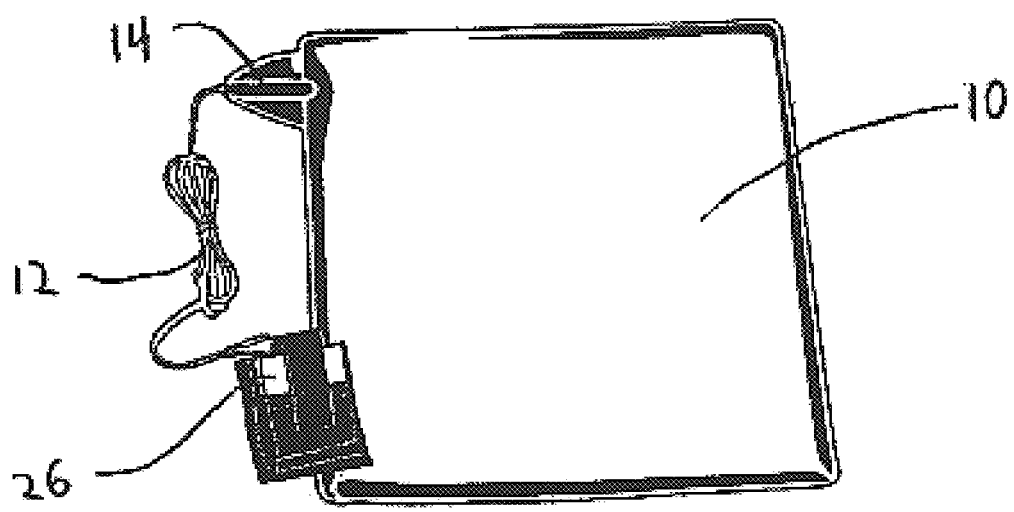
FIG. 8 is a perspective view of the pad connecting to an alarm.

FIG. 8 shows how the pad 10 and cord 12 attach to the alarm 26. The alarm 26 can produce any sound that will warn caregivers of a potential problem. The preferred sound is a unique "tolling bell" sound. The sound is designed to be soft enough so as to not frighten the patient or disturb a roommate, yet loud enough to alert staff members to a potentially dangerous situation. Furthermore, it is preferred that the sound be unique to other sounds in nursing homes or hospitals. In the preferred embodiment, the alarm 26 has an "on/off" switch, so that if patient movement is desired by caregivers, the alarm 26 can quickly and easily be turned off so it will not sound.

The alarm 26 is designed so that it protects patients who try to disable the alarm 26 without the consent of the caregivers. If the patient tries to disconnect the alarm 26 from the pad 10 by pulling the cord 12 out of the alarm 26 base, the alarm 26 will be given. In this regard, a patient could pull the cord 12 out of the alarm 26 base purposefully if he/she wanted to signal a caregiver for any reason. In the preferred embodiment, the alarm 26 base is placed at a distance away from the patient so the patient cannot reach the "on/off" switch without getting off of the pad 10, which would activate the alarm.

FIG. 7 shows the corrugated plastic sheet 22 that lines the inside of the pad 10. This plastic sheet 22 is designed like cardboard in that it provides structural rigidity to the pad 10. This structural rigidity allows the pad 10 to be used on soft mattresses as well as with lighter weight patients.

Figure 5:
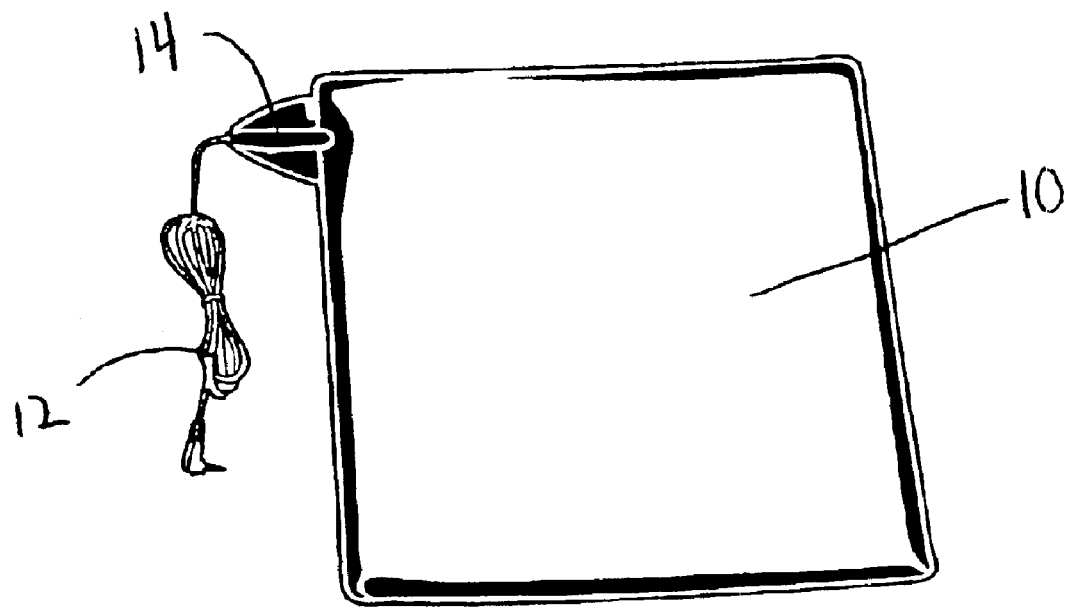
FIG. 5 is a perspective view of the top side of the chair embodiment of the invention.
Figure 6:
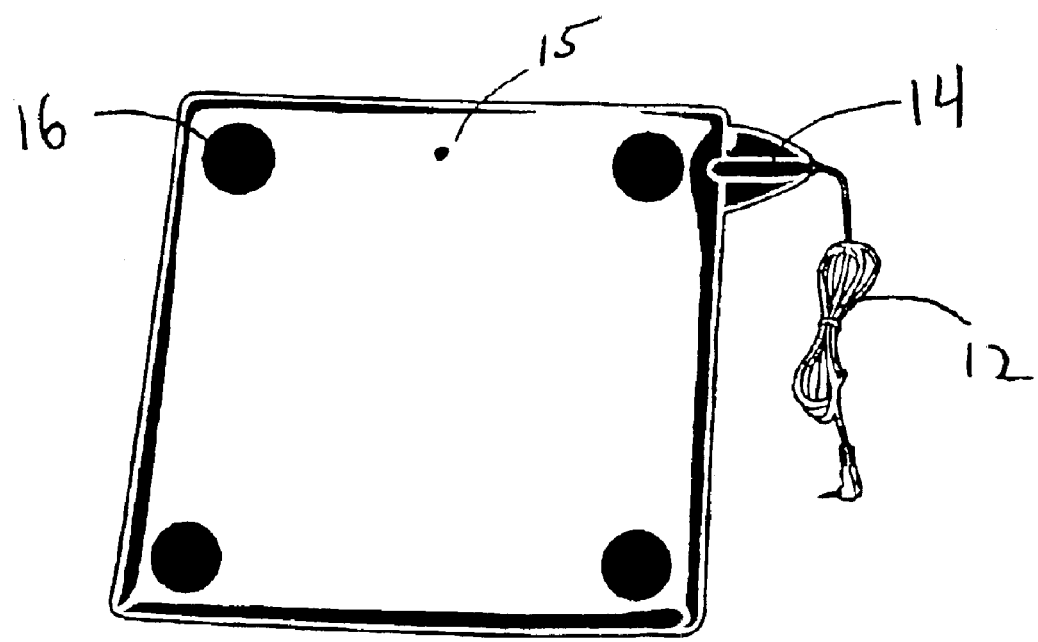
FIG. 6 is a, perspective view of the bottom side of the chair embodiment of the invention.

FIGS. 5 and 6 illustrate a second preferred embodiment of the invention. This embodiment has all of the same characteristics and features as the bed embodiment described above, however, it is smaller so that it easily fits onto a chair. FIGS. 5 and 6 illustrate the top and bottom of the chair pad 10 embodiment of the invention.

A more elaborate or expensive version of the invention may include a different power source, a means for message transmittal to a response center or medical facility, radio transmission from the pad 10 to the alarm 26, or a visual indicator, such as a LED (Light Emitting Diode) that illuminates in conjunction with or separately from the audible alarm. A LED can also be used to warn when the power source is low.

Having thus described the invention in connection with the preferred embodiments thereof, it will be evident to those skilled in the art that various revisions can be made to the preferred embodiments described herein without departing from the spirit and scope of the invention. It is my intention, however, that all such revisions and modifications that are evident to those skilled in the art will be included within the scope of the following claims.

What is claimed is:

1. A personal monitoring device for activating an alarm when weight is lifted from a pad, said device comprising:
   a pad having an interior portion and an exterior portion;
   the exterior portion of the pad being comprised of a water resistant material;
   the interior portion of the pad having a single sheet of circuitry that is folded to create an upper layer of circuits and a lower layer of circuits;
   a layer of resilient material inserted between the upper layer of circuits and the lower layer of circuits; and
   a cord connector for connecting the circuits to an alarm such that when the pad is compressed and the top layer of circuits is in contact with the bottom layer of circuits, the alarm is not activated, but when the top layer of circuits becomes separated from the bottom layer of circuits, the alarm is activated.

2. The personal monitoring device of claim 1 wherein exterior portion of the pad is comprised of Polyvinyl Chloride (PVC).

3. The personal monitoring device of claim 1 wherein the circuits are arranged in a pattern that enables the upper layer of circuits to contact the lower layer of circuits when pressure is applied anywhere on the pad.

4. The personal monitoring device of claim 1 wherein said upper layer of circuits and said lower layer of circuits are enclosed in a plastic film.

5. The personal monitoring device of claim 1 wherein the interior portion of the pad further comprises a corrugated plastic sheet.

6. The personal monitoring device of claim 1 wherein the exterior portion of the pad further comprises at least one opening.

7. The personal monitoring device of claim 1 wherein the exterior portion of the pad further comprises a slip-retardant material.

8. The personal monitoring device of claim 1 wherein the exterior portion of the pad produces a flexible "V" shaped extension along the cord for protecting the interior portion of the pad from liquid.

9. The personal monitoring device of claim 1 wherein the circuits have a built-in time delay to delay the activation of said alarm.

10. The personal monitoring device of claim 6 wherein the opening in the exterior portion of the pad provides a pneumatic time delay to delay the activation of said alarm.

11. The personal monitoring device of claim 1 wherein the circuits are connected to the alarm via radio transmission.

12. The personal monitoring device of claim 1 wherein the alarm is activated when the cord connector is removed from the alarm.

13. The personal monitoring device of claim 1 wherein the alarm issuing means comprises:
   a power source;
   an audible alarm; and
   an "on/off" switch.

14. The personal monitoring device of claim 13 wherein the alarm is light emitting.

15. The personal monitoring device of claim 13 wherein a Light Emitting Diode (LED) is illuminated when the power source is low.

16. A method of monitoring a person comprising the steps of:
   placing a pad underneath a person wherein said pad comprises single sheet of circuitry that is folded to create a top layer of circuits and a bottom layer of circuits, at least one opening, and a layer of resilient material between the layers of circuits;
   using the weight of the person to compress the resilient material so as to force the top layer of circuits and bottom layer of circuits to make contact with each other;
   attaching the pad to an alarm;
   providing a power source to the alarm;
   activating the power source so that if the person's weight is removed from the pad, the resilient material expands as air enters through the opening forcing the top layer of circuits and the bottom layer of circuits to no longer be in contact which thereby activates the alarm.

17. The method of claim 16 wherein the alarm is audible.

18. The method of claim 16 wherein the alarm is visual.

19. The personal monitoring device of claim 1 wherein the circuits are arranged in a grid pattern that enables the upper layer of circuits to contact the lower layer if circuits when pressure is applied on the pad.

20. The personal monitoring device of claim 1 wherein the exterior portion of the pad further comprises a top side and a bottom side, the bottom side of the exterior portion of the pad having slip retardant cushions.

* * * * *